(12) United States Patent
Xie

(10) Patent No.: US 8,027,794 B2
(45) Date of Patent: Sep. 27, 2011

(54) SYSTEM AND METHOD FOR MEASURING PROPERTIES OF LIQUID IN MULTIPHASE MIXTURES

(75) Inventor: Cheng-gang Xie, Sawston (GB)

(73) Assignee: Schlumberger Technology Corporaton, Cambridge, MA (US)

(*) Notice: Subject to any disclaimer, the term of this patent is extended or adjusted under 35 U.S.C. 154(b) by 412 days.

(21) Appl. No.: 12/367,848

(22) Filed: Feb. 9, 2009

(65) Prior Publication Data

US 2009/0204346 A1    Aug. 13, 2009

Related U.S. Application Data

(60) Provisional application No. 61/027,601, filed on Feb. 11, 2008.

(51) Int. Cl.
  *G01F 1/74*    (2006.01)
(52) U.S. Cl. ........................................................ 702/50
(58) Field of Classification Search ..................... 702/50
  See application file for complete search history.

(56) References Cited

U.S. PATENT DOCUMENTS

| | | |
|---|---|---|
| 3,938,738 A | 2/1976 | Nagel et al. |
| 4,044,943 A | 8/1977 | Brown et al. |
| 4,232,549 A | 11/1980 | Migrin et al. |
| 4,282,751 A | 8/1981 | Brown et al. |
| 4,312,234 A | 1/1982 | Rhodes et al. |
| 4,467,659 A | 8/1984 | Baumoel |
| 4,829,831 A | 5/1989 | Kefer et al. |
| 5,007,293 A | 4/1991 | Jung |
| 5,203,211 A | 4/1993 | Jung |
| 5,251,490 A | 10/1993 | Kronberg |
| 5,287,752 A | 2/1994 | Den Boer |
| 5,396,807 A | 3/1995 | Dowty et al. |
| 5,400,657 A | 3/1995 | Kolpak et al. |
| 5,463,906 A | 11/1995 | Spani et al. |
| 5,501,099 A | 3/1996 | Whorff |
| 5,591,922 A | 1/1997 | Segeral et al. |
| 5,654,502 A | 8/1997 | Dutton |
| 5,693,891 A | 12/1997 | Brown et al. |
| 5,719,329 A | 2/1998 | Jepson et al. |
| 5,793,216 A | 8/1998 | Constant |

(Continued)

FOREIGN PATENT DOCUMENTS

EP    0076882 A1    4/1983

(Continued)

OTHER PUBLICATIONS

Atkinson et al: "New generation multiphase flowmeters from Schlumberger and Framo Engineering AS", 17th International North Sea Flow Measurement Workshop, Oslo, Norway, Oct. 25-28, 1999.

(Continued)

*Primary Examiner* — Cindy Hien-Dieu Khuu
(74) *Attorney, Agent, or Firm* — Rachel Greene; Brigid Laffey

(57) ABSTRACT

This disclosure describes measuring properties of a multiphase mixture flowing in a pipe using probes with different sensitivity depths. By generating annular flow of the multiphase mixture in the pipe, the probes may be contacted with the liquid phase of the mixture flowing on an inner-wall of the pipe and apparent permittivities of the annular flow measured by the probes. These measured permittivities may be processed to determine liquid fraction of the annular flow and water-in-liquid ratio of the liquid phase of the annular flow.

21 Claims, 3 Drawing Sheets

U.S. PATENT DOCUMENTS

| | | | |
|---|---|---|---|
| 5,905,208 | A | 5/1999 | Ortiz et al. |
| 6,058,787 | A | 5/2000 | Hughes |
| 6,284,023 | B1 | 9/2001 | Torkildsen et al. |
| 6,575,043 | B1 | 6/2003 | Huang et al. |
| 6,622,574 | B2 | 9/2003 | Fincke |
| 6,719,048 | B1 | 4/2004 | Ramos et al. |
| 6,758,100 | B2 | 7/2004 | Huang |
| 6,831,470 | B2 | 12/2004 | Xie et al. |
| 7,327,146 | B2 | 2/2008 | Simon |
| 7,454,981 | B2 | 11/2008 | Gysling |
| 2003/0011386 | A1* | 1/2003 | Xie et al. ............ 324/694 |
| 2007/0157737 | A1 | 7/2007 | Gysling et al. |
| 2008/0163700 | A1 | 7/2008 | Huang |
| 2008/0223146 | A1 | 9/2008 | Atkinson et al. |
| 2008/0319685 | A1 | 12/2008 | Xie et al. |
| 2009/0114038 | A1 | 5/2009 | Atkinson et al. |
| 2010/0299088 | A1* | 11/2010 | Huang et al. ............ 702/48 |
| 2011/0112773 | A1* | 5/2011 | Atkinson ............ 702/47 |

FOREIGN PATENT DOCUMENTS

| | | |
|---|---|---|
| EP | 0254160 A1 | 1/1988 |
| GB | 1217579 B | 12/1970 |
| GB | 2152213 A | 7/1985 |
| GB | 2177803 A | 1/1987 |
| GB | 2238615 A | 6/1991 |
| GB | 2279146 A | 12/1994 |
| GB | 2300265 A | 10/1996 |
| GB | 2300265 A1 | 10/1996 |
| GB | 2325736 A | 12/1998 |
| GB | 2343249 A | 5/2000 |
| GB | 2343249 B | 1/2001 |
| GB | 2363455 A | 12/2001 |
| GB | 2359435 B | 5/2002 |
| GB | 2363455 B | 10/2002 |
| GB | 2376074 A | 12/2002 |
| GB | 2406386 A | 3/2005 |
| GB | 2420299 A | 5/2006 |
| GB | 2447490 A | 9/2008 |
| GB | 2454256 A | 5/2009 |
| SU | 1337667 A1 | 9/1987 |
| WO | 8902066 A1 | 3/1989 |
| WO | 9108444 A1 | 6/1991 |
| WO | 95/33980 A1 | 12/1995 |
| WO | 9724585 A1 | 7/1997 |
| WO | 00/03207 A1 | 1/2000 |
| WO | 0123845 A1 | 4/2001 |
| WO | 2004106861 A2 | 12/2004 |
| WO | 2004106861 A3 | 2/2005 |
| WO | 2005031311 A1 | 4/2005 |
| WO | 2005040732 A1 | 5/2005 |
| WO | 2007105961 A1 | 9/2007 |
| WO | 2007129897 A1 | 11/2007 |
| WO | 2008029025 A1 | 3/2008 |
| WO | 2008084182 A1 | 7/2008 |
| WO | 2008110805 A1 | 9/2008 |
| WO | 2009037434 A1 | 3/2009 |
| WO | 2009037435 A2 | 3/2009 |
| WO | 2009056841 A1 | 5/2009 |

OTHER PUBLICATIONS

Batchelor: "Steady axisymmetric flow with swirl", An Introduction to Fluid Dynamics, Cambridge University Press, 2000, section 7.5, pp. 543-555.

Clark: "Liquid film thickness measurement", Multiphase Science and Technology, vol. 14, No. 1, 2002, pp. 1-74.

Constant et al: "Multiphase metering using ultrasonics as an alternative approach", Documentation of Multiphase Metering Conference, Mar. 12-13, 1997, The Airport Skean Hotel, Aberdeen, Organised by IBC Technical Services Ltd.

Falcone et al: "Anumet—a novel wet gas flowmeter", SPE Annual Technical Conference and Exhibition, Denver, Colorado, Oct. 5-8, 2003, SPE 84504.

Folgerø et al: "Permittivity measurement of thin liquid layers using open-ended coaxial probes", Measurement Science and Technology, vol. 7, 1996, pp. 1164-1173.

Gibson et al: "Keynote paper—Swirling flow through Venturi tubes of convergent angle 10.5° and 21°", Proceedings of FEDSM2006, 2006 ASME Joint U.S.-European Fluids Engineering Summer Meeting, Miami, Florida, Jul. 17-20, 2006, FEDSM2006-98229.

Greenwood et al: "Self-calibrating sensor for measuring density through stainless steel pipeline wall", Journal of Fluids Engineering, vol. 126, 2004, pp. 189-192.

Gudmundsson et al: "Gas-liquid metering using pressure-pulse technology", SPE Annual Technical Conference and Exhibition, Houston, Texas, Oct. 3-6, 1999, SPE 56584.

Gunarathne et al: "Novel techniques for monitoring and enhancing dissolution of mineral deposits in petroleum pipelines", Offshore Europe Conference, Aberdeen, Sep. 5-8, 1995, SPE 30418.

Hammer: "Flow permittivity models and their application in multiphase meters", Proceedings of Multiphase Metering, IBC Technical Services, Aberdeen Mar. 12-13, 1997.

Hayman et al: "High-resolution cementation and corrosion imaging by ultrasound", SPWLA 32nd Annual Logging Symposium, Midland, TX, USA, Jun. 16-19, 1991, paper KK.

Lynnworth: "Level of liquids and solids", Ultrasonic measurements for process control. Theory, techniques, applications, Academic Press, 1989, chapter 2, section 2.4.3, pp. 58-63.

Lynnworth: "Ultrasonic measurements for process control. Theory, techniques, applications", Academic Press, 1989, pp. 23-27, 30, 32-35, 254-255, 312-317.

Takeda: "Velocity profile measurement by ultrasound Doppler shift method", Int. J. Heat & Fluid Flow, vol. 7, No. 4, 1986, pp. 313-318.

Theron et al: "Stratified flow model and interpretation in horizontal wells", SPE Annual Technical Conference and Exhibition, Denver, Colorado, Oct. 6-9, 1996, SPE 36560.

Willemetz et al: "Instantaneous Doppler frequency measurement and implementation in a multigate flowmeter", Euroson 87, Helsinki, Finland, Jun. 14-18, 1987.

Xie: "Measurement of multiphase flow water fraction and water-cut", American Institute of Physics Conference Proceedings, Jun. 5, 2007, vol. 914, pp. 232-239. Proc. 5th Int. Symp. on Measurement Techniques for Multiphase Flows (5th ISMTMF), Dec. 11-14, 2006, Macau, China.

Bondet De La Bernardie et al. "Low (10-800 MHz) and high (40 GHz) frequency probes applied to petroleum multiphase flow characterization", Measurement Science and Technology, vol. 19, 2008, pp. 1-8.

Fryer et al., "The effect of swirl on the liquid distribution in annular two-phase flow" International Journal of Multiphase Flow, vol. 8, 1982, pp. 285-289.

* cited by examiner

SYSTEM AND METHOD FOR MEASURING PROPERTIES OF LIQUID IN MULTIPHASE MIXTURES

This application claims the benefit of and is a non-provisional of U.S. Patent Application Ser. No. 61/027,601 filed on Feb. 11, 2008, which is incorporated by reference in its entirety for all purposes.

BACKGROUND

This disclosure relates in general to measuring properties of a multiphase mixture flowing in a pipe and, more specifically, but not by way of limitation, to using probes with different sensitivity depths to measure a liquid fraction and a water liquid ratio for a liquid phase of the multiphase mixture.

In the hydrocarbon industry, surface monitoring of oil and gas producing wells is tending towards metering multiphase flows with a wide range of gas volume flow fraction ("GVF"). An example of this are so called wet-gas-wells, where the GVF is typically larger than 95% and the liquid flow rate is typically no more than a few hundred barrels per day. For such production wells, it is often required to measure the gas flow rate and the liquid flow rate, as well as the composition of the liquid phase, e.g. water/liquid hydrocarbon ratio. For wells with GVF<95%, in-line multiphase flow meters may be used to measure flow properties. However, at GVFs above 95%, in-line metering may be problematic and the existing approaches for metering high GVF flows are separation and mixing. The separation approach provides for splitting the flow to be measured/characterized into an almost liquid flow plus an almost gas flow and then separately metering the separated flows using single-phase flow meters. The mixing approach attempts to minimize the slip between the different phases so that the velocity and holdup measurements may be obtained.

The existing methods are largely capable of providing good accuracy for metering gas flows with high GVF, however, the measurements of the liquid flow properties may be inaccurate. The disadvantages of the existing metering methods include increased cost associated with the separation and mixing devices and pressure drop in the pipeline and/or disruption to the flow in the pipeline resulting from the introduction of the separation and/or mixing devices into the pipeline carrying the hydrocarbon mixtures. Additionally, at high GVF, the mixing method may not provide for accurately measuring the holdup and water-in-liquid ratio ("WLR") because the liquid holdup is very low under such conditions.

SUMMARY

In one embodiment of the present invention, a system for measuring properties of a liquid phase of a multiphase mixture flowing through a conduit is provided, the system comprising: a swirl element configured to generate an annular flow of the multiphase mixture; a first probe coupled to an inner-wall of the conduit at a first location, the first probe being configured to contact the liquid phase of the multiphase mixture flowing along the inner wall of the conduit; and a second probe coupled to the inner-wall of the conduit at a second location, the second probe being configured to contact the liquid phase of the multiphase mixture flowing along the inner wall of the conduit; wherein the first and the second probe comprise one of radio-frequency, microwave and millimeter-wave frequency-range electromagnetic sensing probes; the first and second probes are configured to have different sensitivity depths; and the second probe has a second sensitivity depth where the second sensitivity depth is configured to be greater than a depth/thickness of the liquid phase flowing on the inner-wall of the conduit.

In another embodiment of the present invention, a method for measuring properties of a liquid phase of a multiphase mixture flowing in a pipe is provided, the method comprising: swirling the multiphase mixture to generate an annular flow in the pipe, wherein the annular flow comprises a flow of the liquid phase on the inner-wall of the pipe; using a first probe with a first sensitivity depth to measure a first apparent complex permittivity of the annular flow of the liquid phase flowing on the inner-wall of the pipe; using a second probe with a second sensitivity depth to measure a second apparent complex permittivity of the annular flow of the liquid phase flowing on the inner-wall of the pipe, wherein the second sensitivity depth is greater than a depth of the liquid phase flowing on the inner-wall of the pipe; and using a processor to process properties of the liquid phase.

In aspects of the present invention the probes may comprise open ended coaxial probes. The probes may comprise radio-frequency, microwave and/or millimeter-wave frequency-range electromagnetic sensing probes. By using the probes to measure the apparent permittivity of annular flow of the multiphase mixture at two locations in a pipe through which the multiphase mixture is flowing it is possible, in accordance with an embodiment of the present invention, to measure the depth/thickness of the liquid phase of the multiphase mixture flowing in an annular flow on the inner-wall of the pipe, the liquid fraction of the multiphase mixture, the water-liquid-ratio (WLR) of the liquid phase and/or the like.

BRIEF DESCRIPTION OF THE DRAWINGS

The present disclosure is described in conjunction with the appended figures.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DESCRIPTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. Various changes may be made in the function and arrangement of elements of the specification without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, structures, and other components may be shown as components in block diagram form in order not to obscure the embodiments in unnecessary detail. In other instances, well-known processes, techniques, and other methods may be shown without unnecessary detail in order to avoid obscuring the embodiments.

Also, it is noted that individual embodiments may be described as a process which is depicted as a flowchart, a flow diagram, a structure diagram, or a block diagram. Although a flowchart may describe the operations as a sequential process, many of the operations can be performed in parallel or concurrently. In addition, the order of the operations may be re-arranged. Furthermore, any one or more operations may not occur in some embodiments. A process is terminated when its operations are completed, but could have additional steps not included in a figure. A process may correspond to a method, a procedure, etc.

Figure 1:
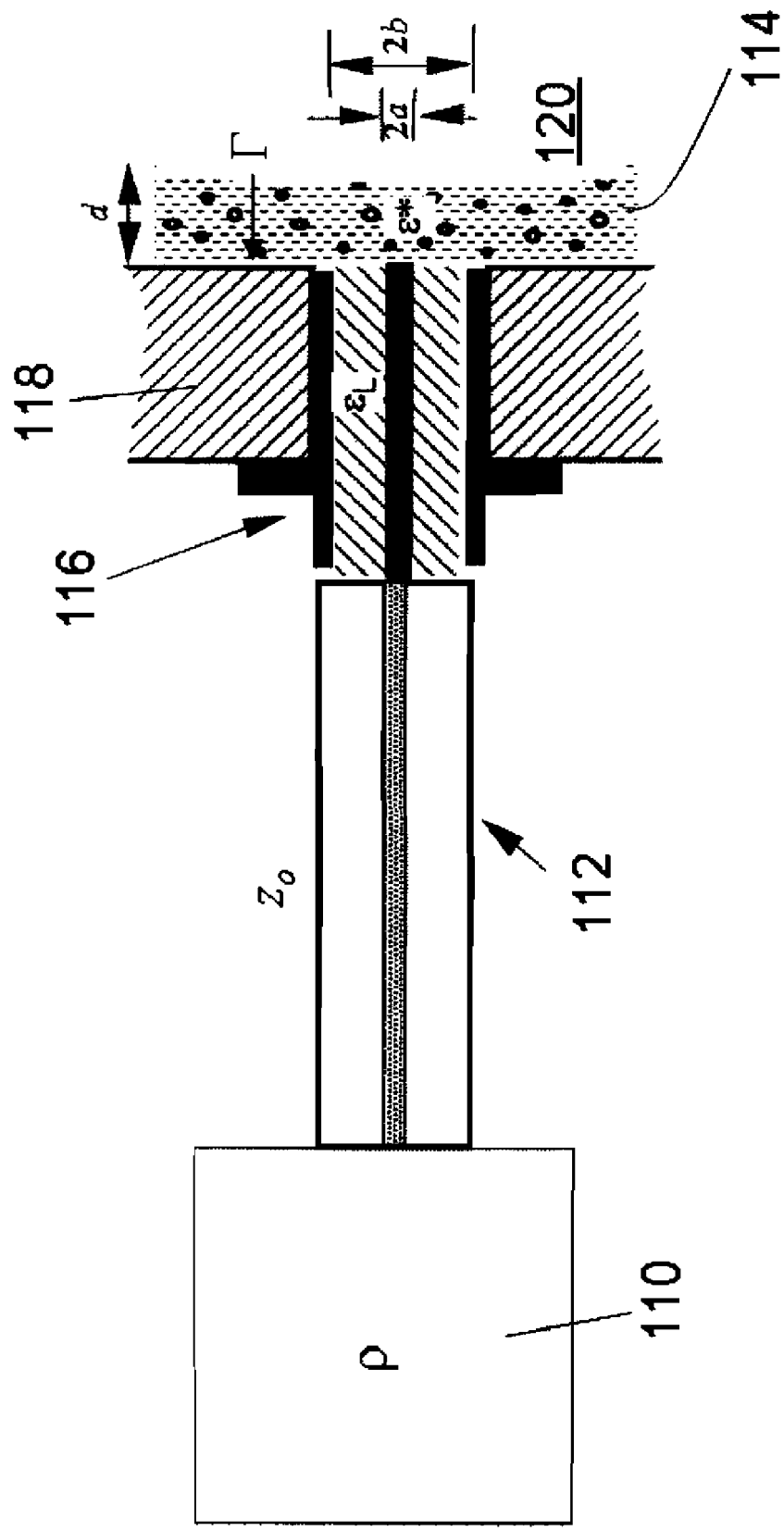
FIG. 1 is a diagram of a coaxial probe installed in a pipe wall, according to an embodiment of the present invention.

FIG. 1 shows a coaxial probe installed in a pipe wall, according to one embodiment of the present invention. As depicted, a single microwave open-ended coaxial probe 116 is flush mounted at the pipe wall 118 and is in contact with a (water-oil) liquid layer 114, shown in this example entrained with gas. The inner conductor of the probe 116 has an outer radius a, an outer conductor of the probe 116 has an inner radius b; the probe insulator (which is thermally and electrically stable, preferably ceramics or glass) is of dielectric constant $e_L$. In the described configuration, the appropriate choice of a, b and $e_L$ determines the characteristic impedance $Z_o$ of probe 116. The probe 116 is connected to a microwave reflectometer 110 by a microwave coaxial cable 112, preferably having the characteristic impedance $Z_o$. The microwave reflectometer 110 may be used to yield measurement of complex reflection coefficient r which is related to complex reflection coefficient G at the probe aperture.

Figure 2:
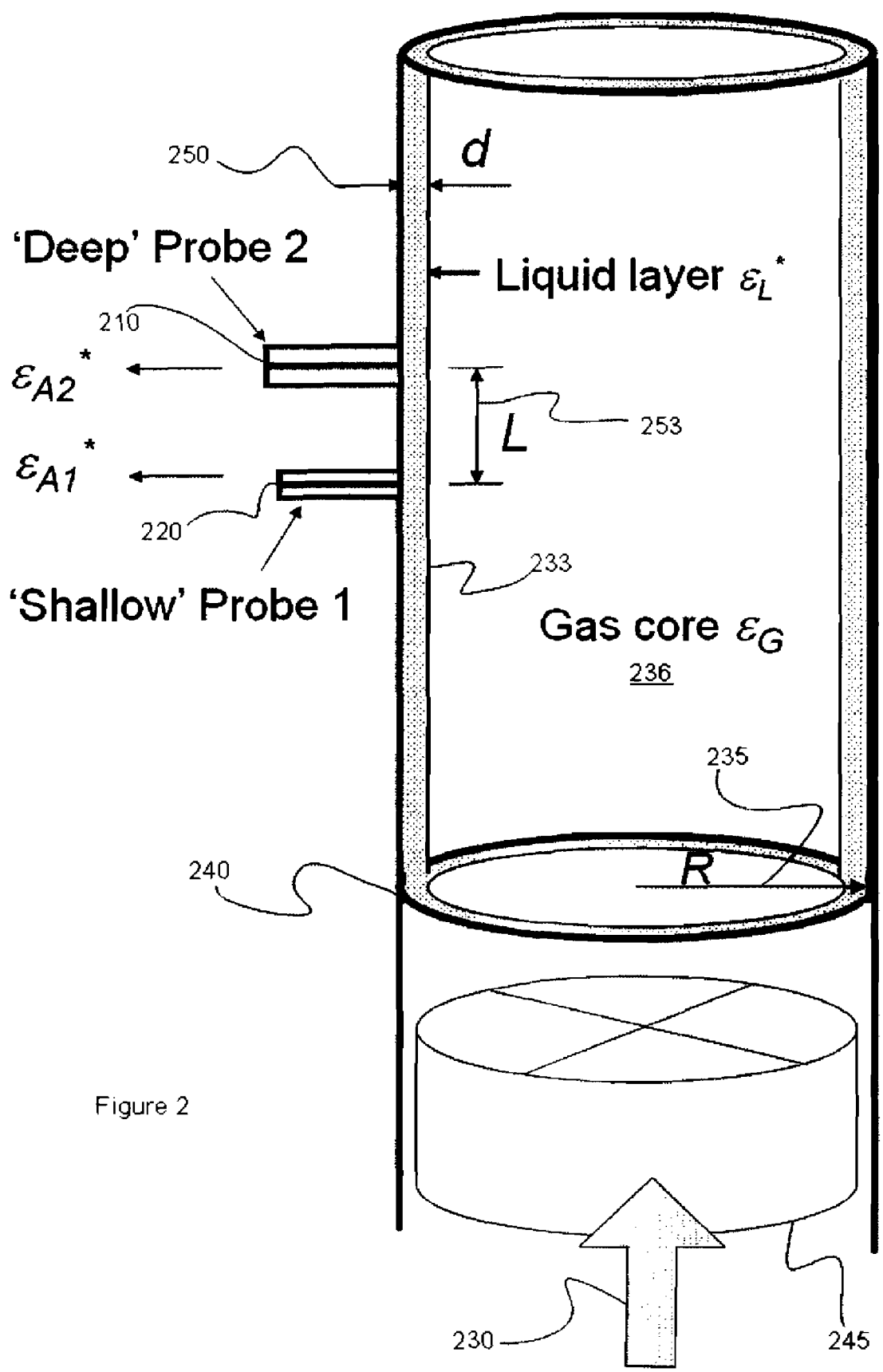
FIG. 2 is a block diagram of a dual probe flow measurement system in accordance with an embodiment of the present invention.

FIG. 2 illustrates a dual probe flow measurement system in accordance with an embodiment of the present invention. In embodiments of the present invention at least one of a deep probe 210 and at least one of a shallow probe 220 may be used to sense properties of a liquid phase of a multiphase mixture 230 flowing in a pipe 240. Merely by way of example, in the hydrocarbon industry, the multiphase mixture may comprise gaseous hydrocarbons and the liquid phase of the multiphase mixture may comprise water and/or oil.

In an embodiment of the present invention, properties of the liquid phase of the multiphase mixture 230 are determined. In certain aspects of the present invention, dual probe flow measurement system may be used to determine properties of the liquid phase where the multiphase mixture 230 comprises a wet-gas flow, and more specifically may be used where the GVF is greater than 95%. In an embodiment of the present invention, the liquid phase of the multiphase mixture 230 may be flowed in an annular layer 233 on an inner-wall of the pipe 240. This may occur naturally in situations where the multiphase mixture 230 is a wet gas and the flow of the wet gas comprises a flow of the liquid phase along the pipe wall and the flow of a gas phase as a gas core along the pipe. In such cases, knowledge of the gas core/liquid annulus flow and/or sensing of the gas core/liquid annulus flow may be used to locate a system in accordance with the present invention and/or to determine when it is applicable to use such a system to determine flow properties of the liquid phase.

In some embodiments, a swirl inducing element 245 may be used to swirl the multiphase mixture 230 so that it swirls as it travels along the pipe 240. Under such swirling flow, the liquid phase generally flows as the annular layer 233 along the inner-wall of the pipe 240 with a gas core 236 flowing through the remainder for the cross-section of the pipe 240. The swirl inducing element 245 may comprise an impeller, a curved element, an angled/tangential inflow into the pipe 240 and/or the like that acts to generate a swirling-type of flow in the multiphase mixture 230. Swirling flow and the generation of such flow is more fully described in co-pending application U.S. Pub. No. 2008/0223146, the entire disclosure of which is incorporated by reference herein for all purposes.

In an embodiment of the present invention, a plurality of pipe-wall mounted radio-frequency (RF), and/or microwave, and/or millimeter-wave frequency-range electromagnetic sensing probes, of the same, different and/or controllable/desired sensitivity depths, may be used to provide, for the measurement of properties of the liquid phase of the multiphase mixture, such as for example the thickness and WLR of the liquid layer flowing on the pipe-wall. In aspects of the present invention, a plurality of pipe-wall mounted open-ended coaxial probes (hereinafter referred to as coaxial probes or microwave probes) of different sensitivity depths may be used to provide, for the measurement of properties of the liquid phase of the multiphase mixture. In one embodiment, coaxial probes such as described in FIG. 1 may be used as the sensing probes.

In one embodiment of the present invention, the deep probe 10 and the shallow probe 220 are coupled with the pipe wall so as to be in contact with annular layer 233. With regard to a coaxial probe, as described above, such a probe may be characterized as having an inner conductor with an outer radius a, an outer conductor with an inner radius b and a probe inner-conductor/outer-conductor insulator, which is thermally and electrically stable and may comprise ceramics or glass, having a dielectric constant $\in_p$. Varying the values of a, b and $\in_p$ of the probe determines the characteristic impedance $Z_o$ (where $Z_o \approx (60/\in_p^{1/2})\ln(b/a)$) of the probe.

The sensitivity depth of an open-ended coaxial probe is about equal to the inner radius b of the outer conductor of the probe. This sensitivity means that the probe is sensitive to the bulk electrical property (electrical permittivity and/or conductivity, or the complex permittivity) of a material within its sensitivity depth. As such, the probe may be used to sense an apparent permittivity $\in_A$ of a material within its sensitivity depth. When the thickness (d) of a liquid layer covering the probe aperture increases beyond the sensitivity depth of the probe, the apparent permittivity $\in_A$ measured by the probe equals the permittivity $\in_L$ of the liquid-layer, for situations where the liquid layer is be backed by a gas layer, such as occurs in a swirling flow and/or annular flow. Consequently, use of a plurality of probes of a plurality of inner radius b (of the coaxial probe outer conductor) will cover a plurality of sensitivity depths into the liquid layer, enabling measuring liquid layer properties comprising complex permittivity, thickness, WLR etc.

In FIG. 2, the annular layer 233 has a depth d 250, the pipe 240 has a radius R 235 and the shallow probe 220 is separated from the deep probe 210 by a distance L 253. Using this configuration and the different sensitivities of the deep probe 210 and the shallow probe 220 the properties of the annular layer 233 may be determined from the apparent permittivities of the annular layer 233 backed by the gas core 236 sensed by the deep probe 210 and/or the shallow probe 220.

In certain aspects of the present invention, probes based on different sensing principles, such as reflection, transmission, resonance and/or the like may be connected to appropriate measurement electronics circuit to determine permittivity and/or conductivity of the annular layer 233. Merely by way of example, a reflection-sensing based coaxial probe, such as described in FIG. 1, may be used in conjunction with an RF/microwave reflectometer, such as described in FIG. 1, by connecting the two apparatuses together using a length of microwave coaxial cable preferably having the same characteristic impedance $Z_o$ as the probe itself. For a plurality of probes, measurements from the probes can be performed sequentially by multiplexing or switching to a single reflectometer, and/or performed in parallel by using a plurality of RF/microwave reflectometers, or in the combination of the two measurement schemes. A reflectometer may operate at single and/or multiple frequencies, where the frequency range depends on the diameter of the coaxial probe aperture. Merely by way of example, a coaxial probe with 7 mm aperture can operate from 200 MHz to 6 GHz. Smaller probes may operate at higher frequencies, with measurement uncertainty typically increasing with increasing frequency.

Microwave reflectometer electronics provides for measurement of an apparent complex reflection coefficient $\rho$ which is related to true complex reflection coefficient $\Gamma$ at the probe aperture plane. The details of the use of microwave open-ended coaxial probes and reflectometers for measuring the complex permittivity ($\in^*$) of an oilfield fluid mixture at a probe aperture have been previously described, for example, in U.S. Pat. No. 6,831,470, entitled "Methods and Apparatus for Estimating On-Line Water Conductivity of Multiphase Mixtures" and in U.S. Pat. No. 7,327,146, entitled "Probe for Measuring the Electromagnetic Properties of a Down-Hole Material", the entire disclosures of which are incorporated herein by reference for all purposes.

In certain aspects of the present invention, the method for measuring the electromagnetic properties of an annular-flow of a multiphase mixture flowing in a pipe may comprise the steps of:

coupling a sensing probe with a pipe wall in contact with the flow;

sending a RF/microwave-frequency input signal into the probe in contact with the flow;

measuring a RF/microwave-frequency output signal reflected by the probe;

measuring a reflection coefficient based on the RF/microwave-frequency output signal;

calculating a complex permittivity value related to the flow based on the reflection coefficient; and repeating the above steps at a different RF/microwave frequency and/or for a different probe.

The method may further comprise a calibration step of using a reflectometer electronic circuit coupled to the probe, the calibration being performed at a determined time interval. The calibration step may comprise successively connecting the electronic circuit to at least three different impedances and measuring the reflected RF/microwave-frequency output signal.

In an embodiment of the present invention, to avoid laboratory-type calibration in field operations and to automatically correct for temperature drift in the electronics circuit and in the open-ended coaxial probe over a wide range of operating temperatures, reflectometer electronics may be designed with a built-in self-calibration arrangement for performing periodic electronics calibration. A self-calibration arrangement may be used to calibrate the electronic circuit and the open-ended coaxial probe itself, at determined time intervals. The self-calibration arrangement may comprise a second coaxial structure, a second switch for connecting to at least three calibration terminations, for example, a short-circuit, an open-circuit and a 50 Ohm termination; the combination of three terminations may be different in order to cover a different impedance range of the fluid measurement coaxial probe (for example a known RC termination can be used). In an aspect of the present invention, the second on-circuit coaxial structure is preferably identical to the fluid measurement coaxial probe to compensate for the changes in the measurement probe length and losses. The details of a self-calibration circuit arrangement for use with a microwave open-ended coaxial probe and a reflectometer electronics have been previously described, for example, in U.S. Pat. No. 6,831,470, entitled "Methods and Apparatus for Estimating On-Line Water Conductivity of Multiphase Mixtures" and in U.S. Pat. No. 7,327,146, entitled "Probe for Measuring the Electromagnetic Properties of a Down-Hole Material", the entire disclosures of which are incorporated herein by reference for all purposes.

Examples and explanations will now be provided regarding complex permittivity (or mixture conductivity and mixture permittivity) determination, in accordance with an embodiment of the present invention. The measured incident and reflected (amplitude and/or phase) signals that are recorded by a reflectometer can be used to derive the complex reflection coefficient at the measurement probe aperture $\Gamma=(Z_c-Z_o)/(Z_c+Z_o)$, which is a measure of the mismatch between the probe's characteristic electrical impedance $Z_o$ and its aperture fluid impedance $Z_c$, where $Z_c=[j\omega C(\in^*)]^{-1}$ and $\omega=2\pi f$ is the angular frequency.

As an illustrative example, the fringe capacitance of a probe may be described as a linear model $C(\in^*)=\in^* C_o+C_f$, where $\in^*=\in'-j\in''$ is the relative complex permittivity of the liquid-layer near the probe aperture and $C_f$ and $C_o$ are capacitance parameters characterizing the probe inner and outer fringe capacitances.

Given the true complex reflection coefficient $\Gamma$ which is the reflected-signal/incident-signal ratio measured at the probe aperture plane, an RF/microwave reflectometer generally measures a different complex reflection coefficient $\rho$ from $\Gamma$, due to, for example, to the length of a microwave cable connecting the measurement probe to the reflectometer, the probe capacitance $C(\in^*)$ and then the fluid complex permittivity $\in^*$ can be derived as $$C(\in^*)=(1-\Gamma)/(1+\Gamma)/(j\omega Z_o)$$

$$\in^*=(C(\in^*)-C_f)/C_o=(1-\Gamma)/(1+\Gamma)/(j\omega Z_o C_o)-C_f/C_o$$

In U.S. Pat. No. 6,831,470, a fluid calibration bilinear model has been described relating the desired complex permittivity $\in^*$ to the actually measured (apparent) reflection coefficient $\rho$, by using three calibration fluids with known, different complex permittivities, without the need of the knowledge of the measurement probe model capacitances $C_o$ and $C_f$. The fluid calibration procedure takes care of electrical-length between the probe and its connector, and all spurious effects (internal reflections, inaccurate mechanical dimensions, etc.). The selection of three-calibration fluids is for example air/water/saline. The derived complex permittivity $\in^*=\in'-j\in''$ is related to the effective conductivity and dielectric properties of the fluid mixture near the probe aperture through $\in^*=\in_m-j\sigma_m/(\omega\in_o)$; here $\in_m$ and $\sigma_m$ are the apparent mixture (relative) permittivity and conductivity; $\in_o\approx 8.854$ pF/m is the (absolute) permittivity of free space.

The sensitivity depth of an open-ended coaxial probe is about equal to the inner radius b of the probe outer conductor, largely independent of the probe operating frequency. Liquids in a wet-gas stream can be centrifuged/swirled on to the pipe wall as a traveling liquid layer. In FIG. 2, the anticipated depth d 250 is less than the sensitivity depth of the deep probe 210 so that different apparent complex permittivities ($\in^*_{A1}$, $\in^*_{A2}$) may be measured by the deep probe 210 and the shallow probe 220. In an embodiment of the present invention, using a model of annular-flow apparent permittivity ($\in^*_A$) as a function of the liquid-layer thickness (d) and the layer permittivity ($\in^*_L$) enables the calculation of depth d 250 and the complex permittivity of the annular liquid layer 233. In certain aspects, from the depth/thickness d 250 a determination of the overall liquid holdup $\alpha_L$ may be made.

Figure 3:
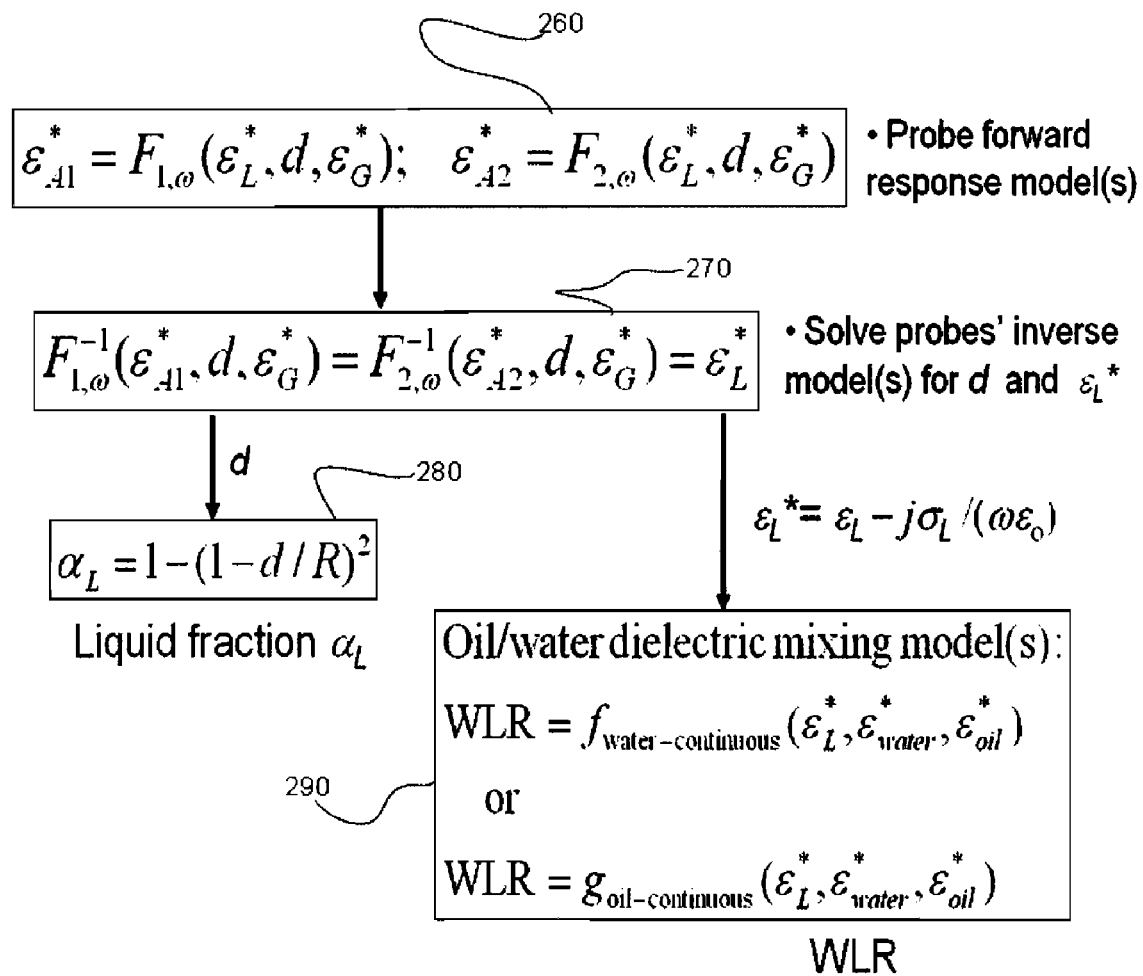
FIG. 3 is a flow diagram of an embodiment of a process for processing the apparent permittivities of an annular flow of a multiphase mixture in a pipe measured by two probes with different sensitivity depths to determine the liquid phase flow properties of the annular flow.

As illustrated in FIG. 3, in accordance with an embodiment of the present invention, apparent permittivities of an annular flow of a liquid phase backed by a gas core of multiphase mixture in a pipe measured by two probes with different sensitivities may be processed to determine properties of the liquid phase of the multiphase mixture, such as flow properties of the annular flow (the annular flow comprising the liquid phase of the mixture, which may also contain some entrained gas). In step 260, the apparent permittivities are measured by the two probes and entered into a processor, the apparent permittivities being equal to functions dependant on the depth and the permittivity of the liquid-layer of the annular flow. In step 270, the two related functions are solved to determine the depth of the liquid layer and the permittivity of the liquid layer comprising the annular flow. In step 280, the depth of the annular-flow liquid layer is processed to determine the liquid fraction. And in step 290, the permittivity of the liquid layer comprising the annular flow is used to determine the WLR using an appropriate permittivity mixing model of a liquid/liquid mixture. The liquid/liquid mixture may be well mixed (of liquid droplets of one phase dispersed in another continuous liquid phase), or may be separated or layered (e.g. of a heavier water annular layer outside of a lighter oil annular layer).

In an embodiment of the present invention, the overall liquid holdup determined from the liquid layer thickness may have little sensitivity to water conductivity change because of the dual-probe arrangement. When oil is the continuous phase, the liquid-layer WLR determination also has little dependence on the water conductivity. For a water-continuous, or an intermittently water-continuous liquid layer, the capability of on-line water conductivity estimate from the complex permittivity, rapidly measured by either/both coaxial probes, will allow an on-line WLR estimate in changing water salinity situations, as described in U.S. Pat. No. 6,831,470, entitled "Methods and apparatus for estimating on-line water conductivity of multiphase mixtures", the entire disclosure of which is incorporated herein by reference for all purposes.

In certain aspects, cross-correlating of the dual-probe measurements may be used to yield the velocity of the liquid layer, giving rise to a liquid flow rate measurement. Cross-correlating of signals from two axially spaced probes of the same sensitivity depth is preferred. As such, in some embodiments, one or more additional probes with a sensitivity depth equivalent to one of the two probes may be used for the cross-correlating method. In other aspects, a microwave Doppler probe flush-mounted at the pipe wall or the like may be used to determine liquid-layer flow velocity. In yet other aspects of the present invention, gas flow rate measurement may be achievable by using other means, such as using a Venturi, given the estimated liquid flow rate and the WLR.

Different probe response models for the determination of fluid permittivity may be used. For example, a bilinear model which uses calibration measurements of complex reflection coefficient on three samples with known permittivities to establish complex permittivity of an unknown sample from the related complex reflection coefficient measurement, in combination with a probe's response model, may be used to estimate the permittivity of a liquid layer when its thickness is known.

At a measurement angular frequency ($\omega$), the apparent permittivity ($\in^*_A$) measured by a probe varies with the liquid-layer thickness d and its permittivity $\in^*_L$; the backing gas-core permittivity $\in^*_G$ is largely considered known, viz.

$$\in^*_A = F_\omega(\in^*_L, d, \in^*_G) \qquad (1)$$

In a dual-probe embodiment of the present invention, when gas is/forms the low-permittivity background material ($\in^*_G$), such as occurs in gas-liquid annular flow in a circular pipe, response model(s) of a plurality of probes (such as provided in equation 1) may be used to determine both the permittivity ($\in^*_L$) and the thickness (d) of the liquid layer of the gas-liquid annular flow, where, as provided in aspects of the present invention (i) two probes of different sensitivity depths are used, and (ii) the thickness of the liquid-layer is smaller than the sensitivity depth of the deeper-sensing probe. In such a dual-probe embodiment of the present invention, the following probes' response relationships may be provided:

$$\in^*_{A1} = F_{1,\omega}(\in^*_L, d, \in^*_G) \qquad (2a)$$

$$\in^*_{A2} = F_{2,\omega}(\in^*_L, d, \in^*_G) \qquad (2b)$$

where $\in^*_{A1}$ and $\in^*_{A2}$ are the apparent permittivities measured by probe 1 and probe 2 with 'shallow' and 'deep' sensitivity depths, respectively. The sensitivity depth of a probe may be designed with a desired characteristic, and may be determined from electromagnetic modeling calculations and/or from experimental measurements.

In an embodiment of the present invention as illustrated in FIG. 1, a dual-probe system may be used for determining liquid layer thickness (d) and liquid layer complex permittivity ($\in^*_L$), given the two apparent complex permittivity measurements ($\in^*_{A1}$ and $\in^*_{A2}$), based on probe response models of equations 2a and 2b. It may be useful to rearrange these equations as follows by equating the inverse form of the probe response functions of equations 2a and 2b, viz.

$$F_{1,\omega}^{-1}(\in^*_{A1}, d, \in^*_G) = F_{2,\omega}^{-1}(\in^*_{A2}, d, \in^*_G) = \in^*_L \qquad (3)$$

In an embodiment of the present invention, a processor or the like may be used to solve, directly or indirectly (e.g. by iteration), the complex-variable equations (on the left of equation 3) to obtain the liquid layer thickness (d). Given d, the liquid-layer fraction $\alpha_L$ in a circular pipe of radius R may be provided as follows:

$$\alpha_L = 1 - (1 - d/R)^2 \qquad (4)$$

The liquid layer complex permittivity $\in^*_L$ may then be determined from the derived d—for example, from the solution of the right two equations of equation 3.

As an example, with the electromagnetic skin depth $\delta \approx (\pi f \mu_o \sigma)^{-1/2} > d$ (when f=1 GHz, $\sigma$=10 S/m, then $\delta \approx 5$ mm; here $\mu_o = 4\pi \times 10^{-7}$ H/m), the apparent permittivity ($\in^*_A$) measured by a microwave coaxial probe varies exponentially with the liquid layer thickness d, with a pre-determined probe model constant (D) that is substantially independent of the measurement frequency and the liquid-layer permittivity $\in^*_L$ $$\in^*_A = (\in^*_G - \in^*_L) e^{-d/D_1} + \in^*_L \qquad (5)$$

In a dual coaxial probe embodiment of the present invention, when gas-liquid forms a gas-liquid annular flow in a circular pipe (See FIG. 2), the empirical model (such as provided in equation 5) of a plurality of probes may be used to determine both the permittivity ($\in^*_L$) and thickness (d) of the liquid layer of the gas-liquid annular flow, where, as provided in aspects of the present invention (i) two probes of different sensitivity depths (probe constants D) are used, and (ii) the thickness of the liquid-layer is smaller than the sensitivity depth of the deeper-sensing coaxial probe. In such a dual-probe embodiment of the present invention, the following two relationships are provided:

$$\in^*_{A1}=(\in^*_G-\in^*_L)e^{-d/D_1}+\in^*_L \quad (6a)$$

$$\in^*_{A2}=(\in^*_G-\in^*_L)e^{-d/D_2}+\in^*_L \quad (6b)$$

where $\in^*_{A1}$ and $\in^*_{A2}$ are the apparent permittivities measured by coaxial probe 1 and probe 2 with probe constants $D_1$ and $D_2$, respectively. Probe constant D may be calculated from electromagnetic modeling and/or determined from experimental measurements.

Equations 6a and 6b can be re-arranged to yield, $$\frac{\varepsilon^*_{A1}-\varepsilon^*_G e^{-d/D_1}}{1-e^{-d/D_1}}=\frac{\varepsilon^*_{A2}-\varepsilon^*_G e^{-d/D_2}}{1-e^{-d/D_2}}=\varepsilon^*_L \quad (7)$$

In an embodiment of the present invention, a processor or the like may be used to solve iteratively the complex-variable equations (on the left of equation 7) to obtain first the liquid layer thickness (d). Given d, the liquid-layer fraction $\alpha_L$ in a circular pipe of radius R may be provided from equation 4. The liquid layer complex permittivity $\in^*_L$ may then be determined from the derived d (e.g. from the right two equations of equation 7).

To measure over a wide range of liquid-layer thickness, more than two probes covering a wider range of sensitivity depths may be used. For example, it is possible to use a 'small' probe with a much shallower sensitivity depth (e.g. b=0.5 mm rather than b=2 mm for a coaxial probe) or to use a 'big' probe with a much deeper sensitivity depth (e.g. b=10 mm rather than b=5 mm). This will facilitate the detection of a thinner or a thicker liquid-layer's true complex permittivity. Multiple dual-probe measurement combinations/embodiments may be realised from multiple (more than two) probe embodiment to enable a wider measurement coverage of liquid-layer thickness, hence covering gas-liquid flows of a wider range of gas volume fractions.

In an embodiment of the present invention, the liquid-layer continuous state (oil or water continuous) may be detected from the magnitude of the calculated liquid-layer complex permittivity $\in^*_L$ (an oil-continuous flow tends to have low values in $\in^*_L$, with the imaginary part of $\in^*_L$ close to nil). In certain aspects of the present invention, by using an appropriate permittivity mixing model generally expressed as below (for a well-mixed, or a layered or other oil/water liquid mixture):

$$WLR=f_{water-continuous}(\in^*_L, \in^*_{water}, \in^*_{oil}) \quad (8a)$$

$$WLR=g_{oil-continuous}(\in^*_L, \in^*_{water}, \in^*_{oil}) \quad (8b)$$

The WLR of the liquid-layer may then be estimated from the derived liquid layer permittivity $\in^*_L=\in_L-j\sigma_L/(2\pi f\in_o)$, given the oil permittivity $\in_{oil}$, water permittivity ($\in_w$ or $\in_{water}$) and/or conductivity ($\sigma_w$ or $\sigma_{water}$) [$\in^*_W=\in_W-j\sigma_w/(2\pi f\in_o)$]. Here $\in_L$ and $\sigma_L$ are the liquid layer effective permittivity and conductivity, respectively; f is the measurement frequency, typically 1 or 2 GHz; $\in_o$=8.854 pF/m.

For a well-mixed oil/water liquid layer, from some example permittivity and conductivity mixing models listed in Table 1 (see E. A. Hammer "Flow permittivity models and their applications in multiphase meters", Proceedings of Multiphase Metering, IBC Technical Services, Aberdeen, 12-13 Mar. 1997), in certain aspects of the present invention, the WLR (denoted as $\gamma_w$) of the liquid-layer may then be estimated from the liquid layer permittivity $\in_L$ and/or conductivity $\sigma_L$, given the oil permittivity $\in_{oil}$ when oil-continuous, or given the water permittivity ($\in_w$) and/or water conductivity ($\sigma_w$) when water-continuous.

TABLE 1

Examples of oil/water mixture permittivity/conductivity mixing models

| | Water-continuous: | Oil-continuous: |
|---|---|---|
| Ramu-Rao: | Forward model: $\varepsilon_L=\varepsilon_w\dfrac{2\gamma_W}{3-\gamma_W}$ $\sigma_L=\sigma_w\dfrac{2\gamma_W}{3-\gamma_W}$ | Forward model: $\varepsilon_L=\varepsilon_{Oil}\dfrac{1+2\gamma_W}{1-\gamma_W}$ |
| | Inverse model: $\gamma_W=\dfrac{3\varepsilon_L}{2\varepsilon_w+\varepsilon_L}$ $\gamma_W=\dfrac{3\sigma_L}{2\sigma_w+\sigma_L}$ | Inverse model: $\gamma_W=\dfrac{\varepsilon_L-\varepsilon_{Oil}}{\varepsilon_L+2\varepsilon_{Oil}}$ |
| Bruggeman: | | Forward model: $\varepsilon_L=\varepsilon_{Oil}\dfrac{1}{(1-\gamma_W)^3}$ Inverse model: $\gamma_W=1-(\varepsilon_{Oil}/\varepsilon_L)^{1/3}$ |

Changes in water conductivity ($\sigma_w$) of multiphase flows may be tracked by interpreting probe complex permittivity measurements, as have been described, for example, in U.S. Pat. No. 6,831,470, entitled "Methods and apparatus for estimating on-line water conductivity of multiphase mixtures", the entire disclosure of which is incorporated herein by reference for all purposes. The estimated water conductivity can be used as an input to a permittivity and/or a conductivity mixing model, enabling the WLR determination of the liquid layer in the changing water salinity situations.

In aspects of the present invention, by keeping the relative errors in the apparent complex permittivities measured by two coaxial probes similar, the determination of the liquid holdup from the liquid-layer thickness estimate may be essentially immune to errors in the measured apparent permittivities. With ±5% relative error in the measured apparent permittivities for both probes, the maximum absolute error in liquid holdup is about ±0.4% for an oil layer (with WLR=0), and the liquid holdup error decreases with increasing WLR of the liquid layer. The liquid holdup determination (from layer thickness, equation 4) is found to have little dependence on water conductivity variation because such a variation will result in a similar effect on the complex permittivities ($\in^*_{A1}$ and $\in^*_{A2}$) measured by both probes, and the solution of the liquid layer thickness d generally comes from an equation with $\in^*_{A1}$ and $\in^*_{A2}$ inputs being near ratio-metric (for example, from equation 7).

In embodiments of the present invention, there is a marked sensitivity of the WLR, derived from the liquid-layer permittivity and from appropriate mixing models as provided in Table 1, to the coaxial probes' measurement errors. With ±5% relative error in the apparent permittivities measured by both coaxial probes, the resulting WLR absolute error ranges from ±1.5% to ±3.5%, for liquid-layer WLR from 0 to 100%.

In certain aspects of the present invention, liquid-layer flow velocity measurements may be determined by cross-correlating the dual-probe data. Cross-correlating of signals from two axially spaced probes of the same sensitivity depth is preferred. In other aspects, a microwave Doppler probe flush-mounted at the pipe wall or the like may be used to determine liquid-layer flow velocity, as have been described, for example, in G.B. Pat. No. 2359435, entitled "Microwave Doppler Flowmeter", the entire disclosure of which is incorporated herein by reference for all purposes. In other aspects, a Venturi or the like may be used to determine a gas flow rate from the liquid flow rate and the WLR.

In an embodiment of the present invention, microwave reflectometer electronics for use with two or more microwave coaxial probes may be configured to have negligible or similar relative measurement errors (including polarity) for one or more combinations of the dual-probe embodiment, since opposing relative errors in the measured apparent complex permittivities for the two probes (e.g. $\delta\in_{A1}=-\delta\in_{A2}=\pm5\%$) may result in large errors in the liquid holdup estimate (from layer thickness d) and in the resulting WLR determination (from layer complex permittivity $\in^*_L$). In certain aspects of the present invention, this may be achieved by using a carefully designed multiplexer for multiplexing combination(s) of two measurement probes to one reflectometer electronics.

It is possible to integrate two or more separate ('shallow' and 'deep') coaxial probes into a single coaxial probe structure of multiple coaxial conductors, and to use a single set of microwave electronics to select, by multiplexing, a coaxial dual-probe ('shallow' and 'deep') combination one at a time for taking complex reflection coefficient measurement. Multiple dual-probe, and/or integrated multiple-probe configurations may be implemented, at different circumference or axial locations around/along a pipe, to assess for example the variation of liquid-layer thickness around the pipe circumference, and/or the variation of liquid-layer velocity at different (radial) depths.

The invention has now been described in detail for the purposes of clarity and understanding. However, it will be appreciated that certain changes and modifications may be practiced within the scope of the appended claims. Moreover, in the foregoing description, for the purposes of illustration, various methods and/or procedures were described in a particular order. It should be appreciated that in alternate embodiments, the methods and/or procedures may be performed in an order different than that described.

What is claimed is:

1. A system for measuring properties of a multiphase mixture flowing through a conduit, comprising:
    a swirl element configured to generate an annular flow of the multiphase mixture;
    a first probe coupled to an inner-wall of the conduit at a first location, the first probe being configured to contact a liquid phase of the multiphase mixture flowing along the inner wall of the conduit; and
    a second probe coupled to the inner-wall of the conduit at a second location, the second probe being configured to contact the liquid phase of the multiphase mixture flowing along the inner wall of the conduit; wherein:
        the first and second probe are configured to have different sensitivity depths; and
        the second probe has a second sensitivity depth where the second sensitivity depth is configured to be greater than a depth of the liquid phase flowing on the inner-wall of the conduit.

2. The system for measuring properties of a multiphase mixture flowing through a conduit in accordance with claim 1, wherein the first and the second probe each comprise open ended coaxial probes.

3. The system for measuring properties of a multiphase mixture flowing through a conduit in accordance with claim 1, wherein the first and the second probe each comprise one of a radio-frequency, a microwave and a millimeter-wave frequency-range electromagnetic sensing probe.

4. The system for measuring properties of a multiphase mixture flowing through a conduit in accordance with claim 1, further comprising:
    a processor in communication with the first and second probes.

5. The system for measuring properties of a multiphase mixture flowing through a conduit in accordance with claim 4, wherein the processor processes a first apparent permittivity of the annular flow measured by the first probe and a second apparent permittivity of the annular flow measured by the second probe to determine a depth of the annular flow of the liquid phase.

6. The system for measuring properties of a multiphase mixture flowing through a conduit in accordance with claim 5, wherein the processor processes the depth of the annular flow to determine a liquid fraction of the multiphase mixture.

7. The system for measuring properties of a multiphase mixture flowing through a conduit in accordance with claim 4, wherein the processor processes a first apparent permittivity of the annular flow measured by the first probe and a second apparent permittivity of the annular flow measured by the second probe to determine a water-liquid-ratio of the liquid phase of the annular flow.

8. The system for measuring properties of a multiphase mixture flowing through a conduit in accordance with claim 4, wherein the multiphase mixture comprises one or more hydrocarbons.

9. The system for measuring properties of a multiphase mixture flowing through a conduit in accordance with claim 1, further comprising:
    a first microwave reflectometer coupled with the first probe by a first microwave coaxial cable.

10. The system for measuring properties of a multiphase mixture flowing through a conduit in accordance with claim 9, further comprising:
    a second microwave reflectometer coupled with the second probe by a second microwave coaxial cable.

11. A method for measuring properties of a multiphase mixture flowing in a pipe, comprising:
    swirling the multiphase mixture to generate an annular flow in the pipe, wherein the annular flow comprises a flow of a liquid phase of the multiphase mixture on the inner-wall of the pipe;
    using a first probe with a first sensitivity depth to measure a first apparent complex permittivity of the annular flow;
    using a second probe with a second sensitivity depth to measure a second apparent complex permittivity of the annular flow, wherein the second sensitivity depth is greater than a depth of the annular flow; and
    using a processor to process properties of the flowing multiphase mixture from the measured apparent complex permittivities.

12. The method for measuring the properties of the multiphase mixture flowing in the pipe in accordance with claim 11, wherein the step of processing the properties of the flowing multiphase mixture comprises using a model of annular-flow apparent complex permittivity as a function of liquid layer thickness and liquid layer complex permittivity and the measured first and the second apparent complex permittivities to process the thickness of the liquid phase or the complex permittivity of the liquid phase.

13. The method for measuring the properties of the multiphase mixture flowing in the pipe in accordance with claim 12, further comprising:
using the processed thickness of the liquid phase to determine a liquid fraction of the multiphase mixture over the pipe cross-section.

14. The method for measuring the properties of the multiphase mixture flowing in the pipe in accordance with claim 12, further comprising:
using a permittivity or conductivity mixing law of a liquid/liquid mixture and the complex permittivity of the liquid phase to determine the water-in-liquid-ratio of the liquid phase.

15. The method for measuring the properties of the multiphase mixture flowing in the pipe in accordance with claim 11, further comprising:
cross-correlating measurements from the first and the second probes to determine a liquid-layer flow velocity.

16. The method for measuring the properties of the multiphase mixture flowing in the pipe in accordance with claim 11, further comprising:
cross-correlating measurements from the first probe and a further probe with an equivalent sensitivity depth to determine a liquid-layer flow velocity.

17. The method for measuring the properties of the multiphase mixture flowing in the pipe in accordance with claim 11, further comprising:
using the liquid-layer flow velocity to determine a liquid flow rate of the liquid phase.

18. The method for measuring the properties of the multiphase mixture flowing in the pipe in accordance with claim 11, further comprising:
measuring a flow rate of a gas phase of the multiphase mixture from the flow rate of the liquid phase, the water-in-liquid-ratio and a flow rate of the multiphase mixture.

19. The method for measuring the properties of the multiphase mixture flowing in the pipe in accordance with claim 17, wherein the flow rate of the multiphase mixture is determined from measurements of differential pressure of the multiphase mixture as it flows through a Venturi.

20. The method for measuring the properties of the multiphase mixture flowing in the pipe in accordance with claim 11, wherein the first and second probe each comprise an open ended coaxial probe.

21. The method for measuring the properties of the multiphase mixture flowing in the pipe in accordance with claim 11, wherein the first and second probe each comprise one of a radio-frequency, a microwave and a millimeter-wave frequency-range electromagnetic sensing probe.

* * * * *